(12) United States Patent
Lee

(10) Patent No.: US 6,413,085 B1
(45) Date of Patent: Jul. 2, 2002

(54) SYSTEM FOR IMPROVING THE APPEARANCE OF TEETH

(75) Inventor: Thomas E. Lee, Grand Terrace, CA (US)

(73) Assignee: Panadent Corporation, Grand Terrace, CA (US)

( * ) Notice: Subject to any disclaimer, the term of this patent is extended or adjusted under 35 U.S.C. 154(b) by 0 days.

(21) Appl. No.: 09/789,028

(22) Filed: Feb. 20, 2001

(51) Int. Cl.⁷ .................................................. A61C 11/00
(52) U.S. Cl. ........................................... 433/56; 433/72
(58) Field of Search ............................ 433/68, 72, 73, 433/55, 56, 59, 215

(56) References Cited

U.S. PATENT DOCUMENTS

| | | | |
|---|---|---|---|
| 2,758,375 A | * | 8/1956 | Badovinac et al. ........... 433/68 |
| 4,449,929 A | * | 5/1984 | Reese ........................... 433/56 |
| 4,610,629 A | * | 9/1986 | Schrems et al. .............. 433/72 |
| 4,659,311 A | * | 4/1987 | Raskin .......................... 433/55 |
| 4,840,564 A | * | 6/1989 | Segal ............................ 433/72 |
| 4,906,186 A | * | 3/1990 | France, Jr. .................... 433/72 |
| 5,360,340 A | | 11/1994 | Rheinberger et al. |

OTHER PUBLICATIONS

Claude R. Rufenacht, Fundamentals of Esthetics, 1992, Quintessence Publishing Co, Inc., Chicago, Illinois, pp. 20–23, 90–93.

* cited by examiner

Primary Examiner—Todd E. Manahan
(74) Attorney, Agent, or Firm—Knobbe, Martens, Olsen & Bear, LLP

(57) ABSTRACT

The disclosed waxing guide is in the form of a thin flat element having a central line formed thereon. The guide is placed beneath the dental cast with the central line centered between maxillary central incisors on the dental cast. Lines spaced outwardly from the central line indicate the apparent width of the central incisor, the adjacent lateral incisor, and the adjacent canine tooth and first bicuspid, when viewed from the front. Each of the spaces has the same ratio of 1:1.618 with the adjacent spaces.

8 Claims, 11 Drawing Sheets

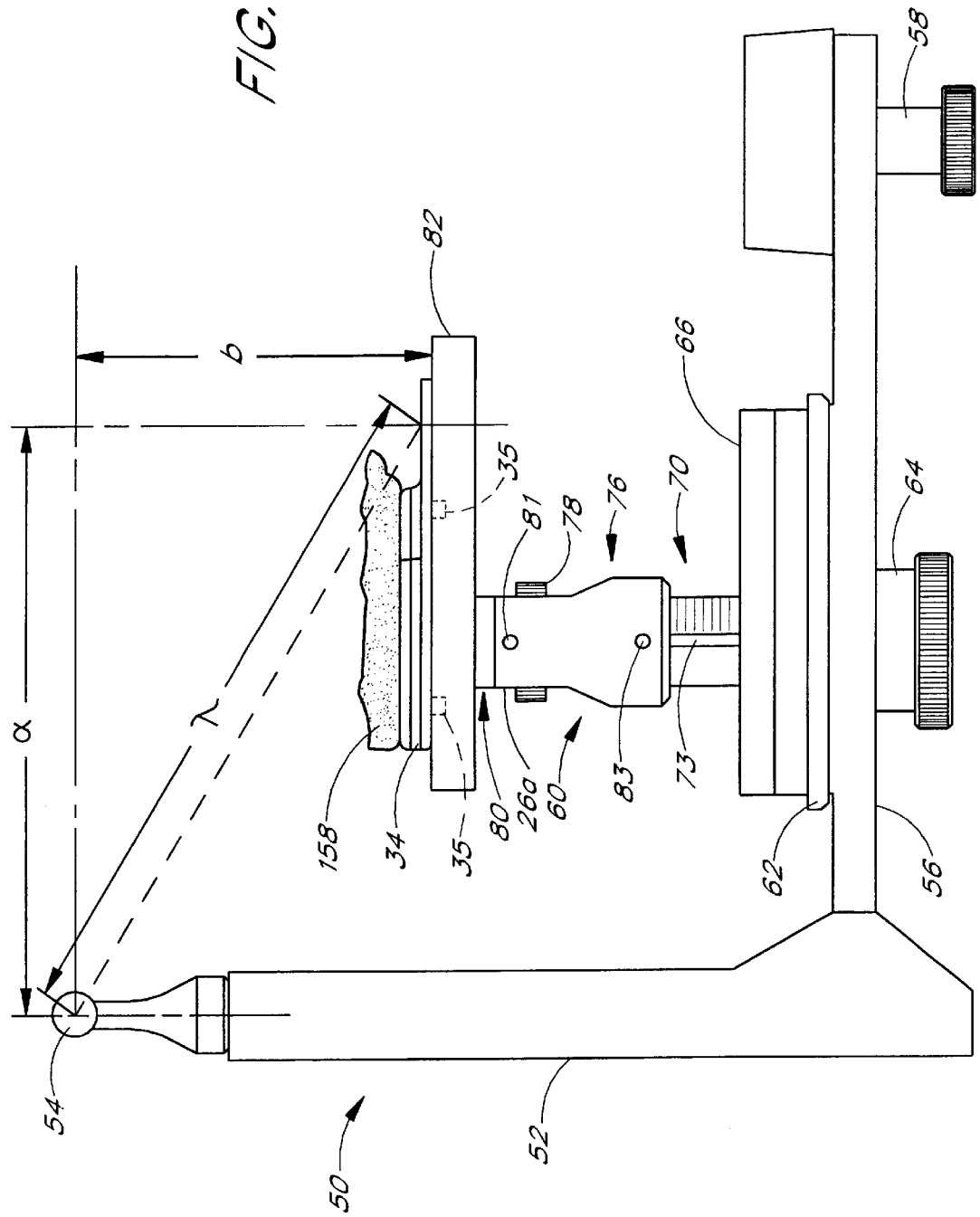

SYSTEM FOR IMPROVING THE APPEARANCE OF TEETH

FIELD OF THE INVENTION

The present invention relates to a system for assisting dentists and dental technicians in the forming and shaping of artificial frontal teeth so as to improve the appearance of a person's smile.

BACKGROUND OF THE INVENTION

In recent years, more attention is being paid to improving the aesthetic aspects of a patient's teeth at the same time that the functional aspects are being improved. Particular attention is being directed to the anterior maxillary teeth inasmuch as they are most visible when a person smiles. It is desirable that the left and right central incisors be approximately bisected by the person's mid-sagittal plane. In addition, it has been recognized that there is a desirable ratio between the width of the adjacent teeth, and that this ratio surprisingly is about the same for adjacent teeth. That is, it is considered desirable that the ratio of the width of the central incisor to the adjacent lateral incisor is the same as the ratio between the width of the lateral incisor to that of the adjacent canine tooth.

This proportion or ratio is believed to be common for many relationships of the human body and it also applies to the beauty of other objects. This is referred to in literature as the "golden number" or "golden proportion" or "golden ratio." This ratio is 1:1.618 or 0.618:1. For example, if the width of the central incisor is the unit 1.618, the width of the adjacent lateral incisor should be 1, and the similar ratio should apply between the lateral incisor and the adjacent canine.

In the making of a cap for a tooth, such as a lateral incisor, at least the visible portions of the tooth are removed and replaced by material shaped to provide the desired appearance. This is typically accomplished by applying wax to the tooth stump, and shaping the wax to create the desired shape of the tooth. The wax model is then used to create a mold in which the cap is to be formed. It is desired that a tool or guide be provided which will assist the dentist or technician in the waxing operation.

SUMMARY OF THE INVENTION

Briefly stated, a waxing tool or guide is provided for forming artificial teeth. The guide is preferably in the form of a thin flat element to be mounted on a support, which is preferably in the form of a platform mounted to the lower frame of a dental articulator. The element forming the guide is provided with markings on its upper surface that indicate a desired relationship for a person's anterior maxillary teeth. Preferably, this desired relationship between adjacent teeth is the above-mentioned golden proportion or ratio. Since the width of a central maxillary incisor varies, a set of guides can be provided, for example, with width changes in half mm changes, varying from 7 to 10 mm.

In use, a maxillary dental cast of the patient's maxillary teeth is mounted on a frame such as the upper frame of a dental articulator with the cast being mounted in a known relationship with respect to a platform supporting the waxing guide in a relationship that simulates the patient's maxillary teeth. This can perhaps be accomplished with more than one technique, but in a preferred approach, a face bow analyzer is provided having a bite fork adapted to be positioned within a patient's mouth between the upper and lower teeth. An upper index tray is mounted on the upper surface of the bite fork and a lower index tray is secured to the lower surface of the bite fork. A line on the upper surface of the upper index tray is aligned with the incisal edges of the central incisors on a dental cast. This so-called incisal line is utilized as a reference for mounting a dental cast in the articulator. Dental impression material is applied to the index trays, and the assembly is positioned in the patient's mouth and lightly gripped by the patient's teeth while the dentist grips portions of the face bow extending out of the patient's mouth. The patient's incisors are aligned with the incisal line on the upper surface of the upper index tray. The face bow is then adjusted to a horizontal position and properly aligned with the patient's sagittal plane. The face bow is then held in that position while the impression material hardens.

After that, the upper index tray is mounted on the above-mentioned platform which in turn is mounted on the lower frame of a dental articulator. The incisal line on the tray is aligned with a corresponding incisal line on the platform. The incisal line on the platform is either at a known distance or an average distance from the hinge axis of the dental articulator which corresponds to the distance between the incisal line and the hinge axis of the patient. The dental cast is then positioned in the upper index tray and secured to the upper frame of a dental articulator in a known manner. The dental cast is then in position to have the dental caps or other prosthetic element formed in wax. The upper index tray is removed from the mounting platform and is replaced by the waxing guide. The waxing guide is positioned so that a central line on the guide is aligned with the sagittal plane or dental midline of the dental cast and an incisal line on the guide is aligned with the appropriate incisal line on the mounting platform. With the dental cast positioned close to the waxing guide, the dentist or technician is then in position to form the desired artificial tooth or cap utilizing the guide as an alignment element so as to form the artificial tooth or cap with the desired proportion in relation to the adjacent teeth.

BRIEF DESCRIPTION OF THE DRAWINGS

FIG. 4 is a side elevational view of the lower frame of a dental articulator illustrating an upper index tray from FIGS. 1 and 2 mounted on a platform assembly supported on the articulator frame.

DETAILED DESCRIPTION

Figure 1:
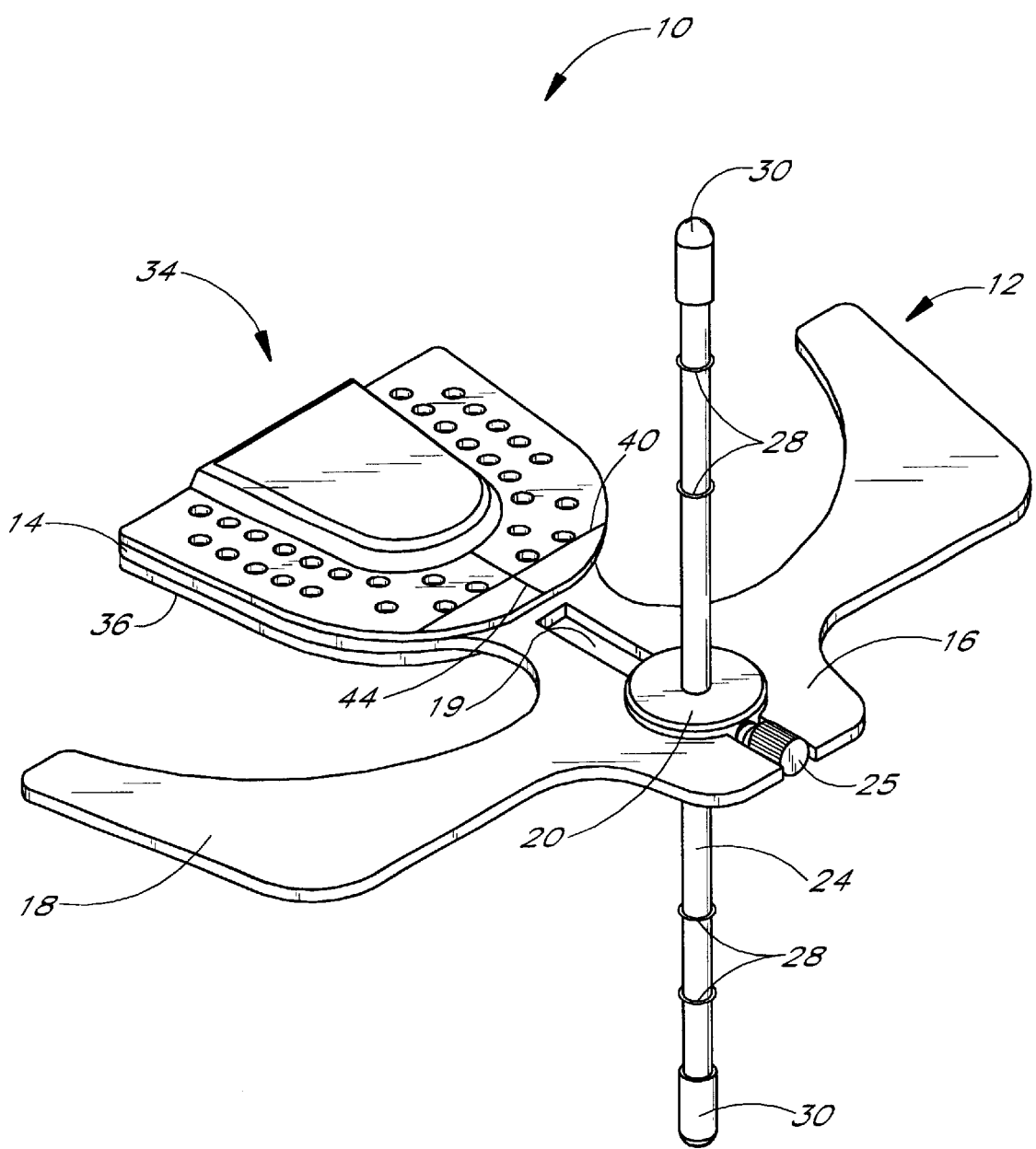
FIG. 1 is a perspective view of an analyzer face bow assembly of the invention.
Figure 2:
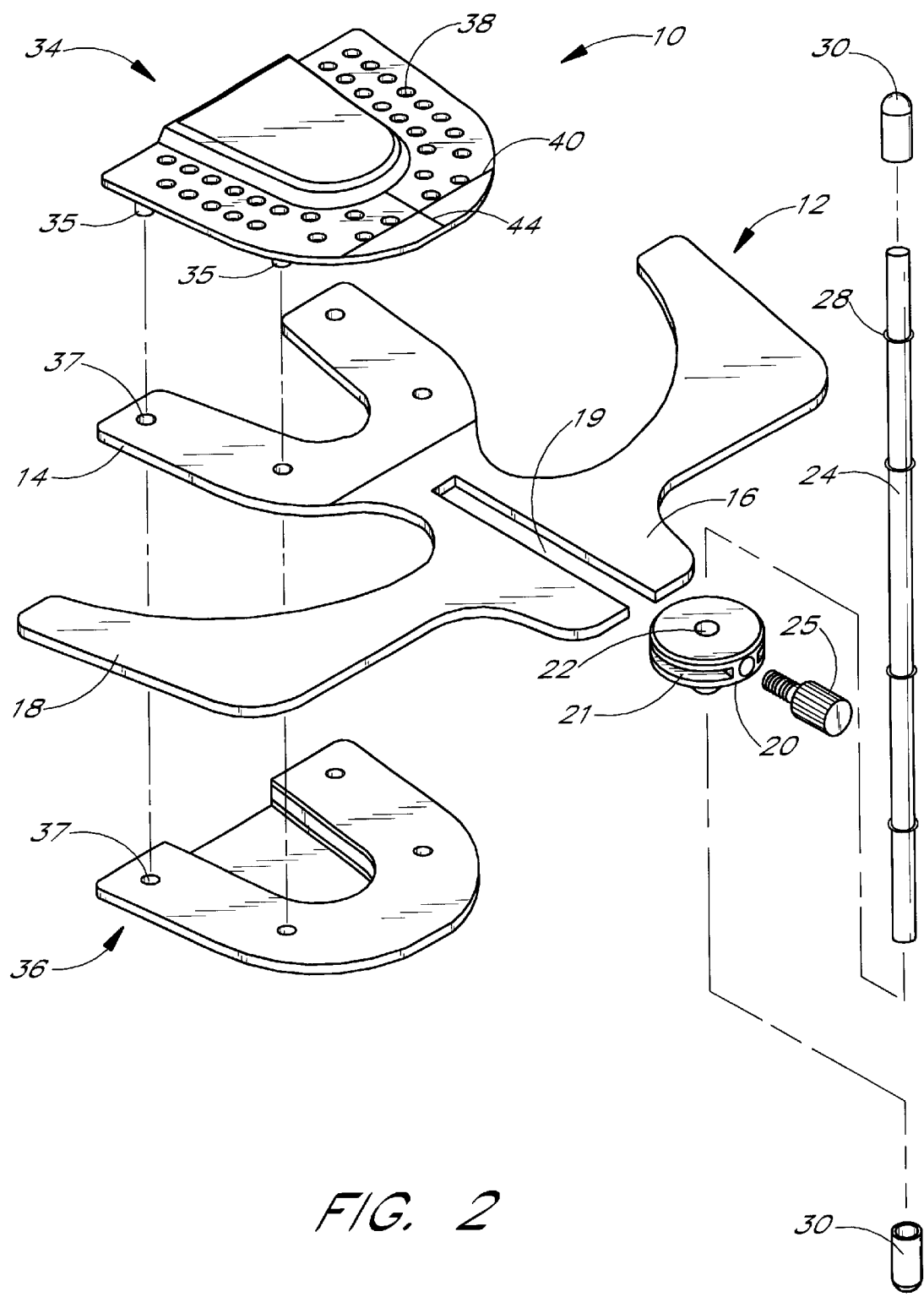
FIG. 2 is an exploded perspective view of the assembly of FIG. 1.

Referring to FIGS. 1 and 2, there is illustrated an analyzer face bow assembly 10, the primary component of which is a face bow 12. The face bow is a multi-function element preferably having a thin flat configuration made of rigid material such as a suitable metal or plastic. It includes a generally U-shaped bite fork or plate 14 sized to mate with a patient's teeth or gums when the jaws are clamped on the plate. The closed forward end of the bite fork leads to a central forward portion 16, and a pair of wings 18 which extend laterally outwardly from the portion 16. The wings are spaced from the bite fork inasmuch as the bite fork 14 is adapted to fit within the patient's mouth and the wings 18 are intended to surround the forward portion of a person's face spaced from the face. The wings 18 could be referred to as handles since they are gripped by the operator when the bow 12 is being installed, adjusted and removed. The central portion 16 includes an elongated straight slot 19 that extends forwardly from the center of the bite fork 14 and opens to the front edge or forward portion 16 of the face bow 12.

A disk-shaped holder 20, which includes grooves 21 on its sides is sized to slide within the slot 19. The holder is formed with a central hole 22 sized to receive a vertical indicator rod 24. This positions the rod 24 perpendicular to the flat bow 12. One or more tubular markers 28 slides on the upper and the lower end of the rod. A protective cap 30 is placed on both ends of the rod 24 safety. A thumb screw 25 fixes the rod relative to the holder 20.

Figure 3:
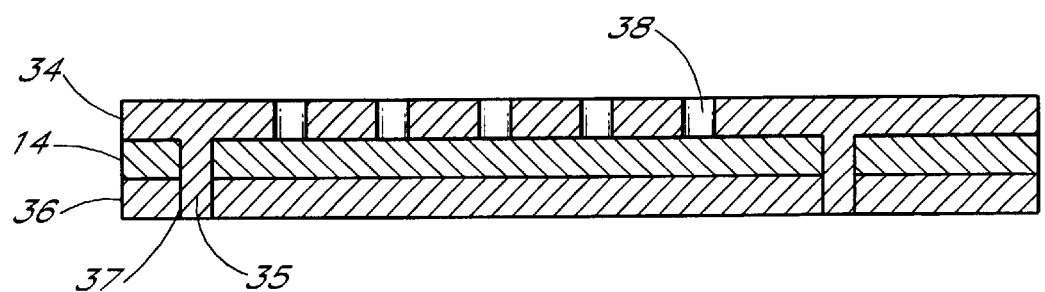
FIG. 3 is cross-sectional view of the index trays positioned on the bite fork portion of the assembly of FIGS. 1 and 2.

The assembly 10 also includes an upper index tray 34 and a lower index tray 36. The upper index tray includes four downwardly extending pins or projections 35 sized 5 to fit within four mating holes 37 formed in the bite fork 14, as seen in FIG. 3. The projections 35 are long enough such that they protrude through the bite fork 14 and fit within four mating holes 37 in the lower index tray 36.

The upper index tray 34 and lower index tray 36 are also provided with a number of small holes or indentations 38 for receiving bite registration material such as impression compound. If desired, the holes 38 can be made frusto-conical in shape, having a smaller diameter at its upper end and a larger diameter at its lower end with tapered sides in-between to help capture impression material. The upper surface of the upper tray has a marking 40 referred to as an incisal line, and has a central line 44 which is perpendicular to and bisects the incisal line 40.

FIG. 4 illustrates the lower frame 50 of a dental articulator, which includes a vertical frame member 52 topped by a pair of balls 54, one of which is shown in FIG. 4. The ball centers define a hinge axis. A horizontal lower frame member 56 is connected to the lower portion of the vertical member 52 and is supported on its forward end by a leg 58. A mounting platform assembly 60 is mounted on a magnetic base plate 62 secured to the lower frame member 56 by a fastener 64.

Figure 5:
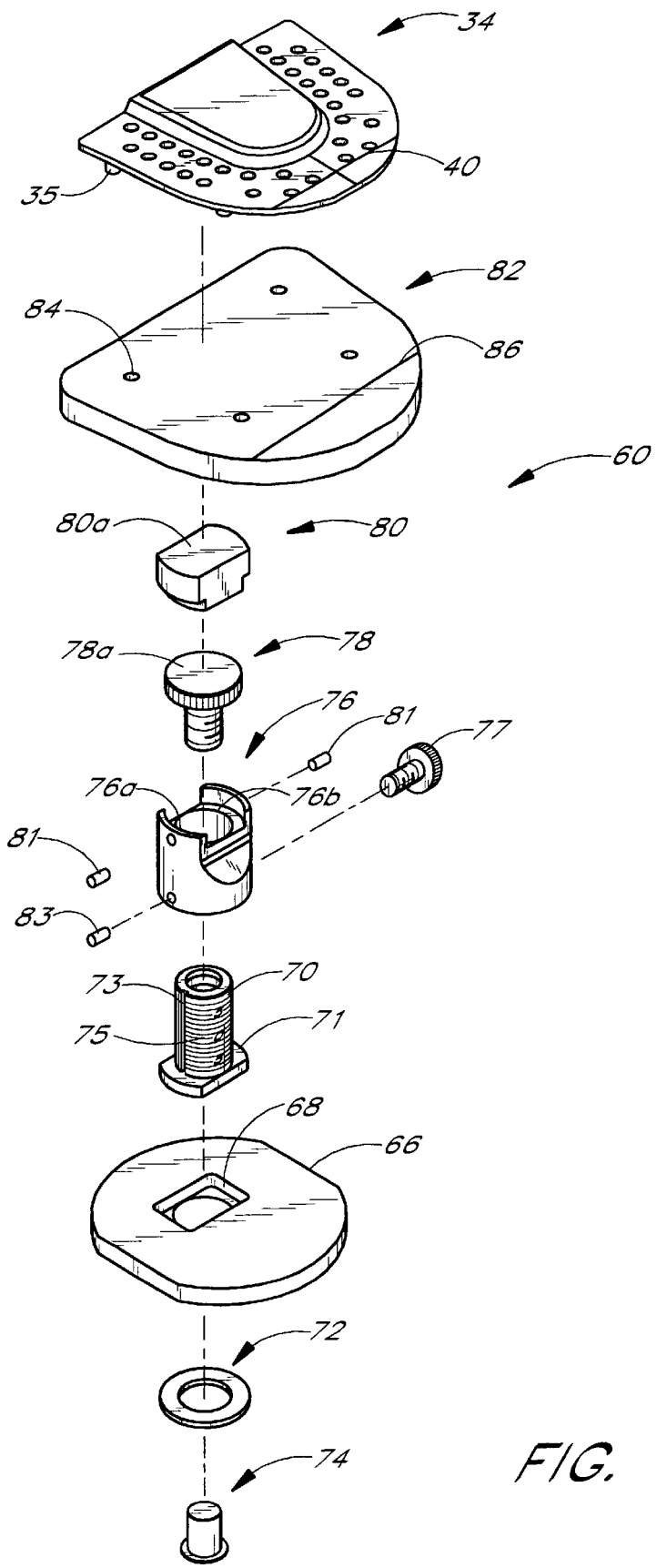
FIG. 5 is an exploded perspective view of the components of the mounting platform of FIG. 4 and the upper index tray of FIG. 2.

Referring to FIGS. 4 and 5, the mounting platform assembly 60 includes a lower base plate 66 having a generally rectangular recess 68 in its upper surface. A tubular support column 70 formed with a generally rectangular base 71 fits within the recess 68 and prevents the column from rotating. The column 70 is locked to the plate 66 by means of a ferrous metal washer 72 and fastener 74 which extends through a hole in the base plate 66 and threads into the interior of the support column 70. The fastener 74 and the washer 72 adhere to the magnetic mounting plate 62 and fit within a recess in the lower surface of the base plate 66. A support collar 76 adjustably slides onto the upper end of the column 70 and is supported by an adjustment screw 78 threaded into the upper end of the column 70. The head 78a of the adjustment screw 78 fits into a recess 76a in the upper end of the collar 76 and engages a shoulder 76b in the recess. The screw head is captured in the collar 76 recess by the lower end of a connector 80 that fits within the recess 76a and is attached to the collar 76 with dowel pins 81. A generally rectangular head 80a on the connector 80 forms an interference fit within a mating recess in the bottom surface of a mounting platform 82.

Thus, rotating the adjustment screw 78 raises or lowers the platform 82. A pin 83 mounted in the collar 76 extends into an axially extending groove 73 in the exterior of the column 70 to prevent rotation of the collar 76. The exterior of the column has a scale or markings 75 to indicate the vertical adjustment. A locking thumb screw 77 further locks the collar 76 to the column 70 after the vertical adjustment is made.

The platform is positioned in a known relationship with respect to the hinge axis, through the balls 54 which correspond to a patient's hinge axis, and the incisal edge. For proper mounting with the upper index tray 34, the platform 82 preferably has four spaced holes 84 that align with the four projections 35 extending downwardly from the upper index tray 34. The mounting platform 82 preferably has an incisal line 86 marked thereon for alignment with the index tray incisal line 40. However, if only an average incisal line-to-hinge axis distance of 100 mm is used, the line on the platform may not needed. The line 40 on the upper index tray 34 and line 86 on the platform 82 may of course be marked in any fashion, such as grooves, solid or dashed lines, etc.

Figure 6A:
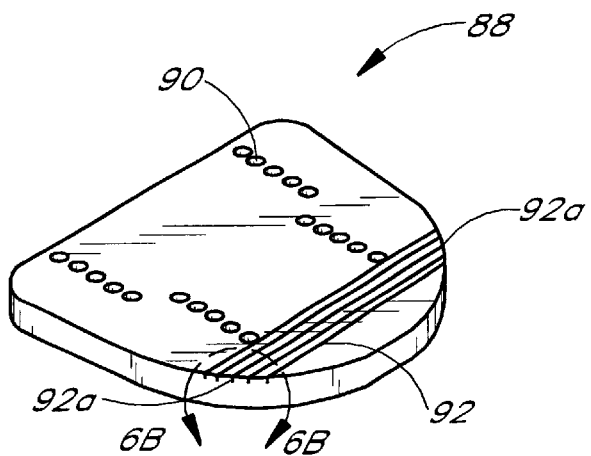
FIG. 6A is a perspective view of an alternate mounting platform of FIG. 5.
Figure 6B:
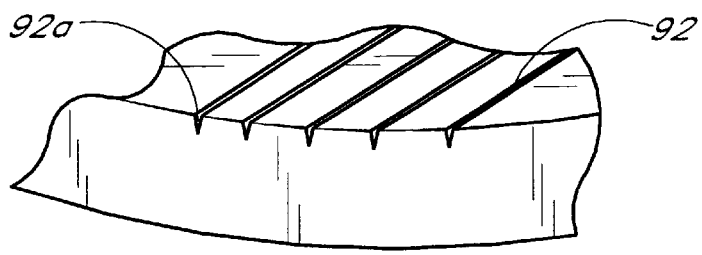
FIG. 6B is an enlarged view of the portion 6B—6B in FIG. 6A.

FIG. 6A illustrates an alternate mounting platform 88. It has five sets of four holes 90 and five spaced incisal lines 92. This enables the index tray 34 to be mounted to the mounting platform 88 in five different positions, such as 90 mm, 95 mm, 100 mm, 105 mm, 110 mm, from a patient hinge axis, such as an incisal line 92. Note also that instead of or in addition to, the outer edges of the lines 92 of the platform 82 and line 40 on the upper index tray 34 can be grooved or notched as shown at 92a to mark the edges of the line as seen in FIG. 6B.

Figure 7:
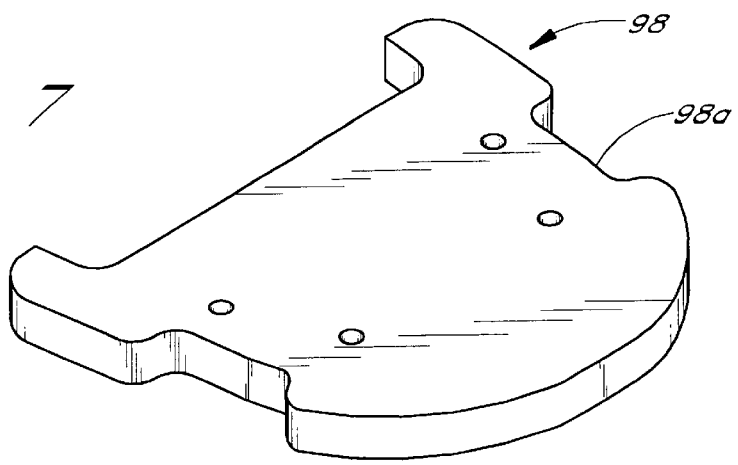
FIG. 7 is a perspective view of another alternate mounting platform of FIG. 5.

FIG. 7 illustrates another form of a mounting plate 98 wherein the sides of the plate are recessed at 98a to facilitate separating an index tray from the plate.

Figure 8:
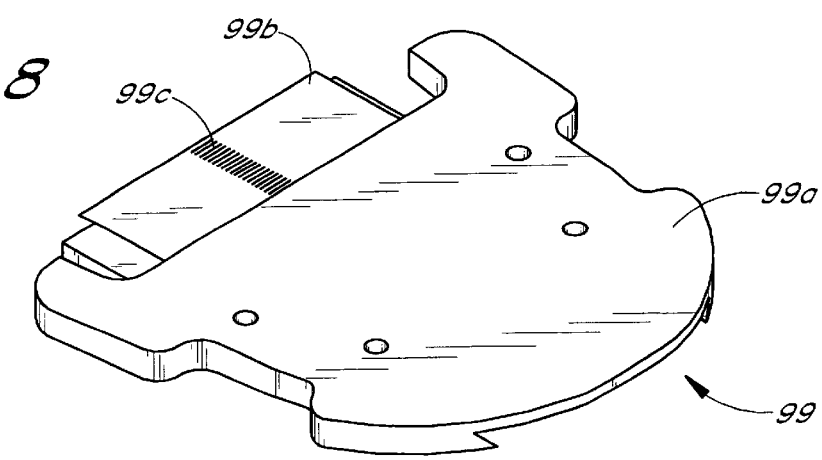
FIG. 8 is a perspective view of a horizontally adjustable platform.
Figure 9:
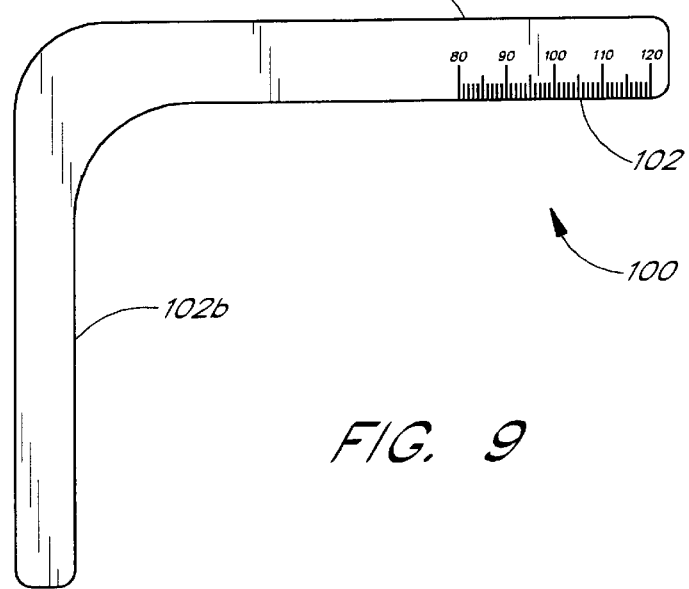
FIG. 9 is a plan view of a tool used to measure a hinge axis-maxillary incisal line distance.

FIG. 8 illustrates an alternate form of a mounting plate 99 that can be horizontally adjusted instead of or in addition to being vertically adjustable. An upper portion 99a is slidably mounted on a lower portion 99b, which can be fixed to the connector 80, shown in FIG. 5. Scale lines 99c indicate the position of the upper portion 99a with respect to the lower portion 99b. A lock screw or other means (not shown) may be provided to lock the two portions together after adjustment.

Operation

Before starting, if a specific axis-incisal distance is to be used, the operator can move the patient's jaw about the temporomandibular joints to locate the approximate hinge axis of the mandible. The operator can measure the distance from this located patient's hinge axis to the patient's maxillary incisal edge and record that distance on the patient's chart, for use in connection with the index tray or in connection with the adjustable mounting platform. If a specific axis-incisal distance is to be used, the operator can measure either forward or backward from the average 100 mm incisal line marked on the upper index tray, and mark the index tray with a new specific axis-incisal line that corresponds with the actual distance measured on the patient.

A patient's axis-incisal distance may be measured by a suitable tool 100 such as that shown in FIG. 8. As seen, the tool has a 90° flat shape, with one arm 100a having distance or scale markings 102 marked thereon. In use, the inner edge of the unmarked arm 102b is placed against the lower edge of the patient's maxillary incisors and the arm 100a is placed so that the markings are adjacent the patient's hinge axis. The distance from the incisal line to the axis can then be observed and recorded.

In use, the vertical indicator rod 24 is connected to the analyzer bow 12 by sliding the rod holder 20 into the slot 19 on the bow. Next, an upper index tray 34 is mounted to the bite fork portion 14 of the analyzer bow 12 with its depending or protruding pins 35 extending into the mating holes 36 on the bite fork portion 14. Those pins extend through the bite fork plate and extend into corresponding holes 37 in the lower index tray 36. Thus, the two index trays 34, and 36 are sandwiched or firmly secured to the bite fork portion 14 of the analyzer bow 12. Soft bite registration material, that is, an impression compound or other suitable material, is placed on both the upper and lower occlusal surfaces of the index trays 34 and 36. Care should be taken not to cover the incisal line on the index tray that will be used with the bite registration material.

Before positioning the analyzer bow with respect to the patient, the patient should sit erect on a backless stool and look straight ahead. Preferably, the patient is looking into a mirror, to make it easier for the patient to maintain that desired position. The analyzer bow assembly 10 is then to be mounted to the patient by positioning the bite fork portion 14 into the patient's mouth. The patient's incisal edge of the maxillary incisors should be aligned with the incisal line marked on the upper surface of the index tray. The patient should be instructed to bite lightly into the compound to register impressions of the patient's teeth and to help the operator support the analyzer bow.

Figure 10:
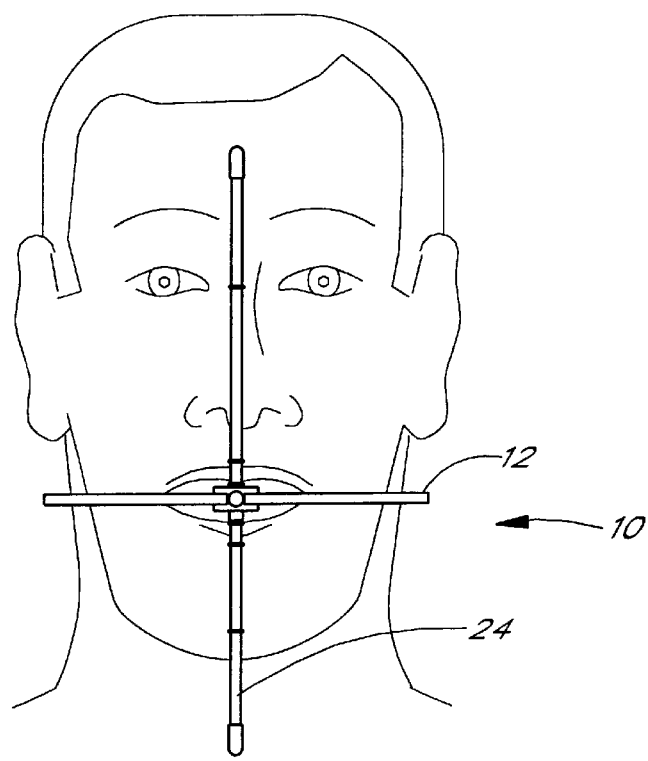
FIG. 10 is a schematic view illustrating the positioning of the face bow of FIG. 1 on a patient from the frontal view.

The vertical indicator rod 24 is then slid rearwardly close to the patient's face within slot 19 of the analyzer bow 12. The analyzer bow assembly 10 is adjusted so that the vertical indicator rod 24, when viewed from the front is aligned with the central mid-sagittal plane through the patient's head, as in FIG. 10. This is done by the operator gripping the wings 18 of the analyzer bow 12 and moving the bow as necessary relative to the patient's teeth and face. That is, the patient is still sitting erect and the bite registration material is still soft such that the index trays mounted on the analyzer bow can be adjusted to make the indicator rod be vertical and centered or aligned to the patient's mid-sagittal when viewed from the front of the patient.

Figure 11:
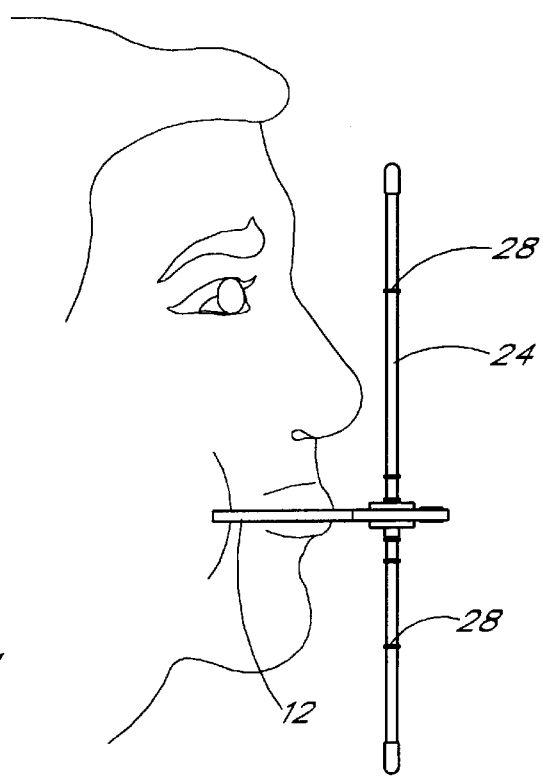
FIG. 11 is a schematic view illustrating the positioning of the face bow of FIG. 1 on a patient from a profile view.

The bow is then viewed from the side, as in FIG. 11, so as to get a profile view, and the bow is adjusted so that it appears horizontal and the rod is vertical. If desired, levels can be added to or incorporated into the wings of the bow to verify or facilitate the leveling action. The analyzer bow is then held in this desired orientation as the bite registration material hardens. The bow now horizontal and the indicator rod now vertical are aligned with respect to the patient's cranium in all three planes of space related to an average 100 mm or specific axis to incisal edge distance.

While the analyzer bow assembly 10 is still mounted to the patient, the patient should be instructed to smile to enable the operator to measure the height of the lip commisures from the upper surface of the upper index tray 34 of the analyzer bow, that is, the distance that the corners of the smile rise above the index tray attached to the analyzer bow. This measurement should be recorded and transferred to the dental cast when mounted in a dental articulator. The height of the eyes, nasal-labial point, incisal edge, the chin, and other specific facial landmarks can also be marked on the vertical indicator rod to evaluate facial proportions. The slidable collars or O-rings 28 can also be used to mark these facial landmarks on the vertical indicator rod.

The patent's mouth can then be opened to permit the operator to carefully remove the analyzer bow assembly 10. The lower index tray 36 can then be removed from the bite fork and discarded. The upper index tray 34 is also removed and sent to the laboratory to be used with the mounting platform as assistance in mounting a dental cast to the dental articulator.

Figure 12:
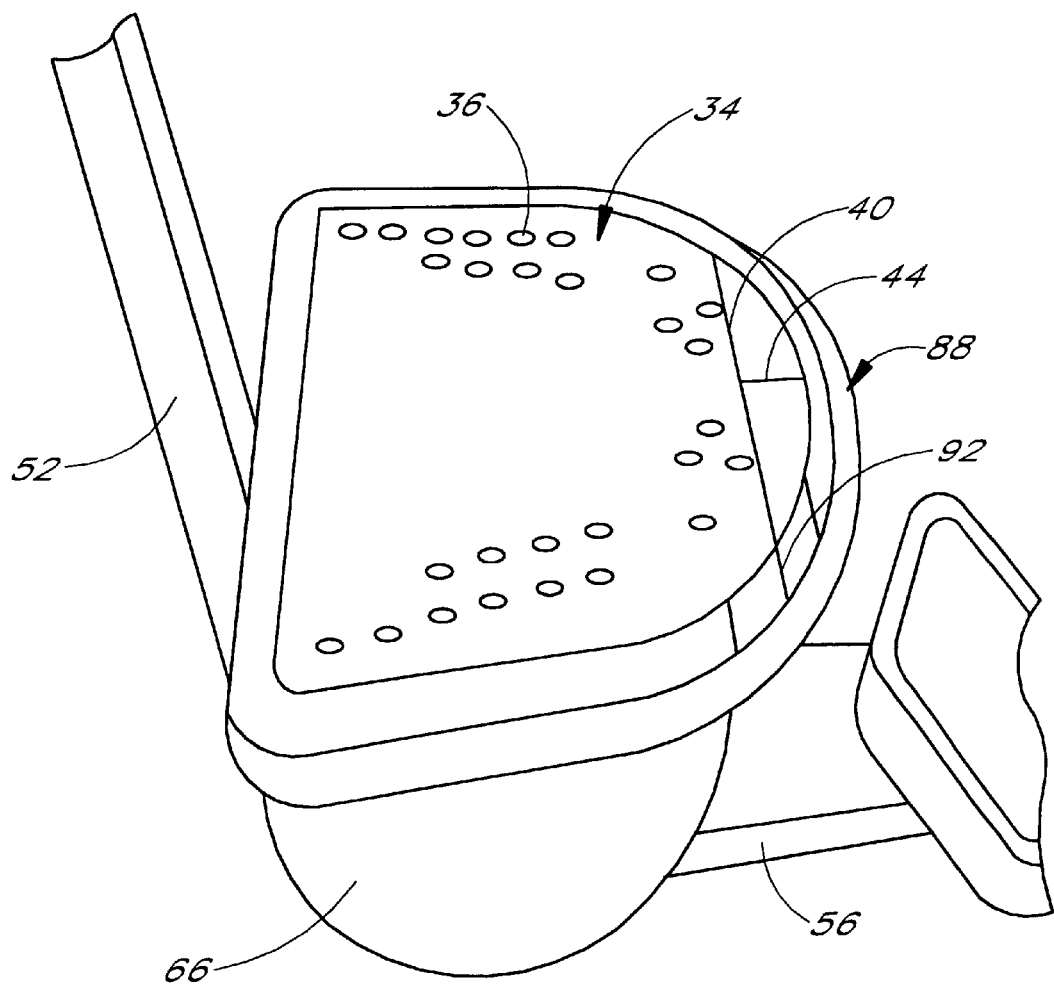
FIG. 12 is a schematic view illustrating the alignment of the upper index tray on the mounting platform attached to the lower frame of a dental articulator.

The adjustable mounting platform assembly 60 is mounted on the lower frame 50 of the dental articulator. The vertical height of the platform 82 is adjusted as desired with the adjustment screw 78 and locked in place with the lock screw 77. If the patient's specific axis-incisal distance was marked on the upper tray and is used, or an average value of 100 mm is used for the distance between hinge axis through the condyle balls 54 on the articulator and the incisal line on the mounting platform, the platform 82 with the single incisal line 86 can be employed, since there would be no adjustment. However, an adjustable mounting platform 88 shown in FIG. 6 could be utilized to orient the index tray in the dental articulator, that best corresponds to the distance from the patient's hinge axis to the maxillary incisal edge. An average value for the distance λ from the hinge axis to the incisal line on a patient is about 100 mm, and that is the dimension used on the upper index tray and on the articulator. The horizontal distance α from the hinge axis to the incisal line on the platform 82 is preferably about 87 mm. The height of the platform above the articulator frame member 56 is preferably centered between the upper and lower frames of the articulator. In a preferred arrangement, the height β is about 60 mm. This equal spacing between the frames of the articulator and the dental casts allows room for magnetic mounting plate systems, pindex systems, dental implants and other procedures. FIG. 12 illustrates the tray properly mounted on the platform (without the impression material).

Figure 13:
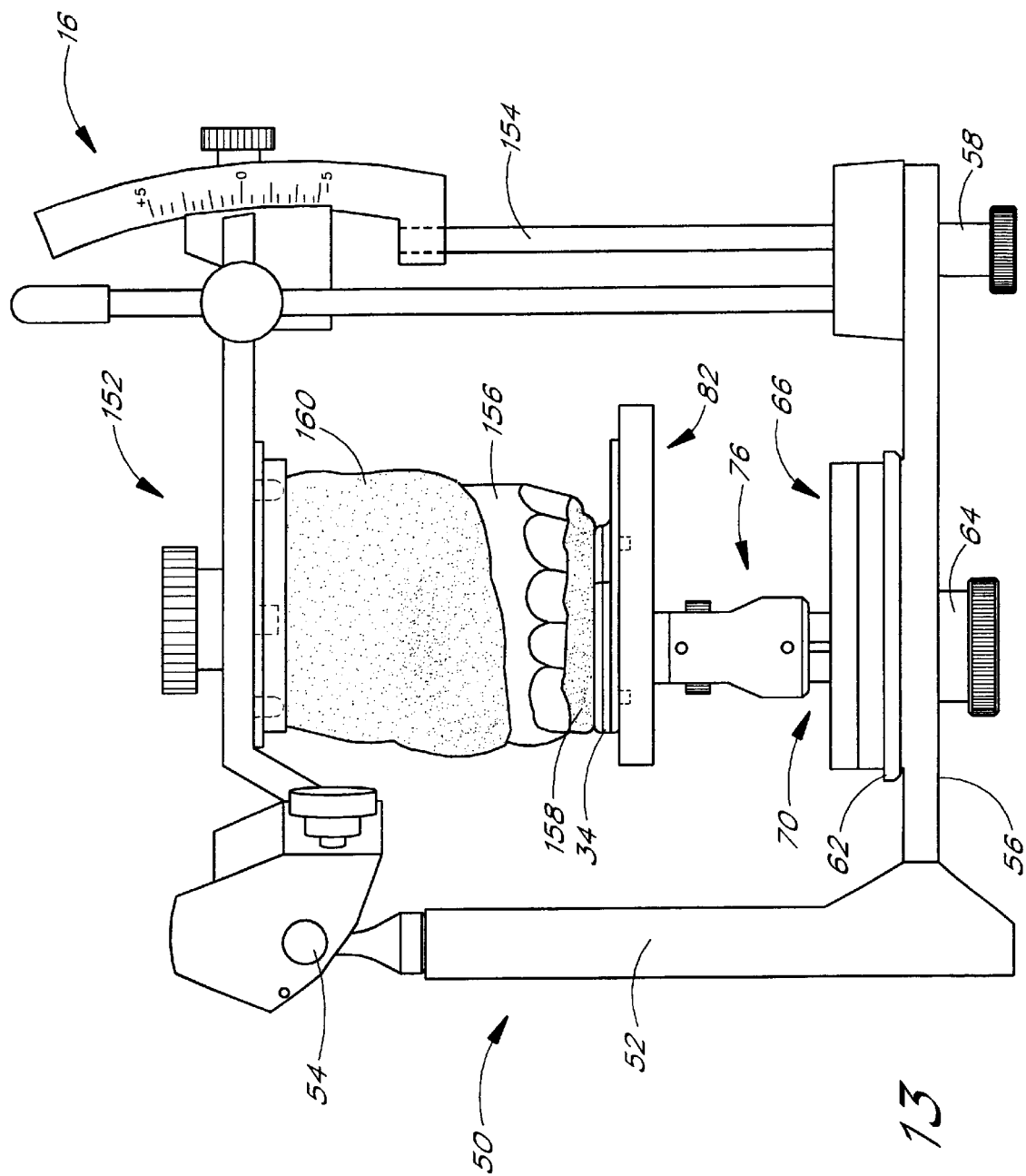
FIG. 13 is a schematic view of an upper dental cast mounted on the index tray in an articulator.

The index tray is now in condition to be used for mounting the patient's maxillary dental cast 156 to the articulator 50. This is accomplished in a known manner. Typically, as seen in FIG. 13, the upper frame 152 of an articulator is positioned on the lower frame 52 axis balls 54 with an incisal pin 154 supporting the forward end of the upper frame being set to zero, which corresponds to a horizontal orientation. The patient's maxillary cast 156 is then positioned on the impressions that are in the bite registration material 158 adhered to the index tray 34, and plaster 160 is utilized to connect the dental cast to the upper frame of the dental articulator.

In shaping the artificial teeth to be formed on the dental cast, the previously recorded information regarding the patient's facial features can be employed to enhance the aesthetic appearance of the prosthetic being formed. For example, the height of the lip commisures can be measured up from the index tray and marked on the dental cast to help evaluate the height of the teeth to enhance the person's smile to the curvature of the lips. Further, the vertical indicator rod can be utilized and analyzed for best considering the length of the incisor or vertical dimension of occlusion in relation to other facial proportions. The mounting platform can be adjusted vertically in millimeters to a desired incisor length. That is,.with the dental cast supported by the upper frame of the articulator and the incisal pin, and the platform lowered a desired amount, the length of the incisors could be increased to be aligned with the incisal line on the platform.

Figure 14:
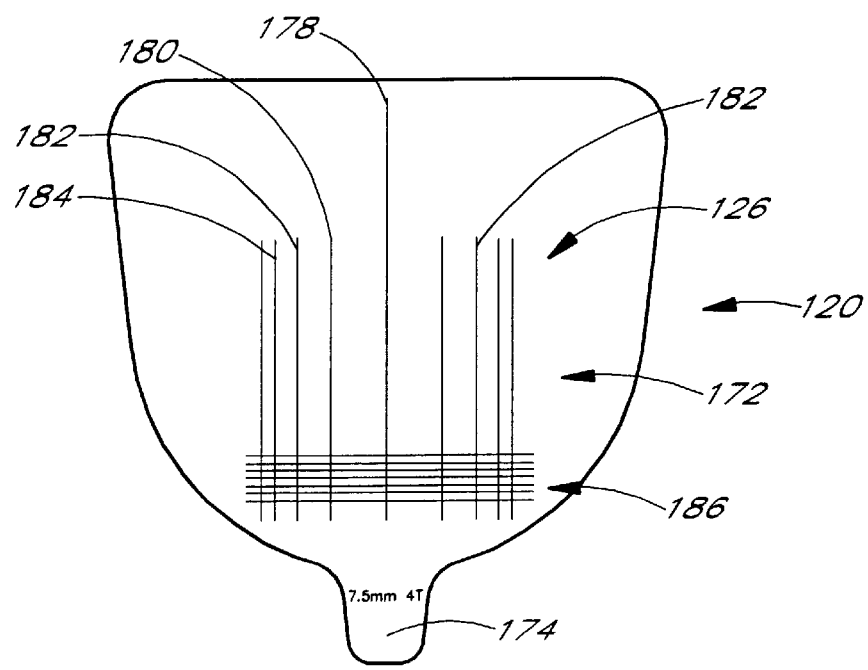
FIG. 14 is a plan view of one of the seven waxing guides of the invention.
Figure 15:
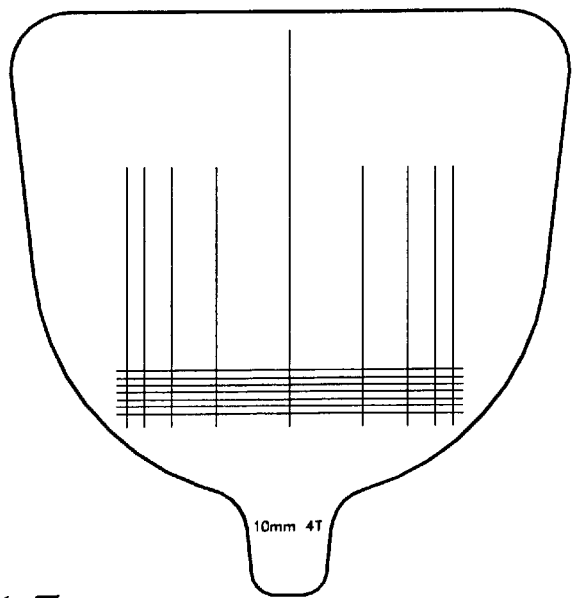
FIG. 15 is a plan view of another waxing guide having indicator lines with spacing different from that of the guide of FIG. 14.
Figure 16:
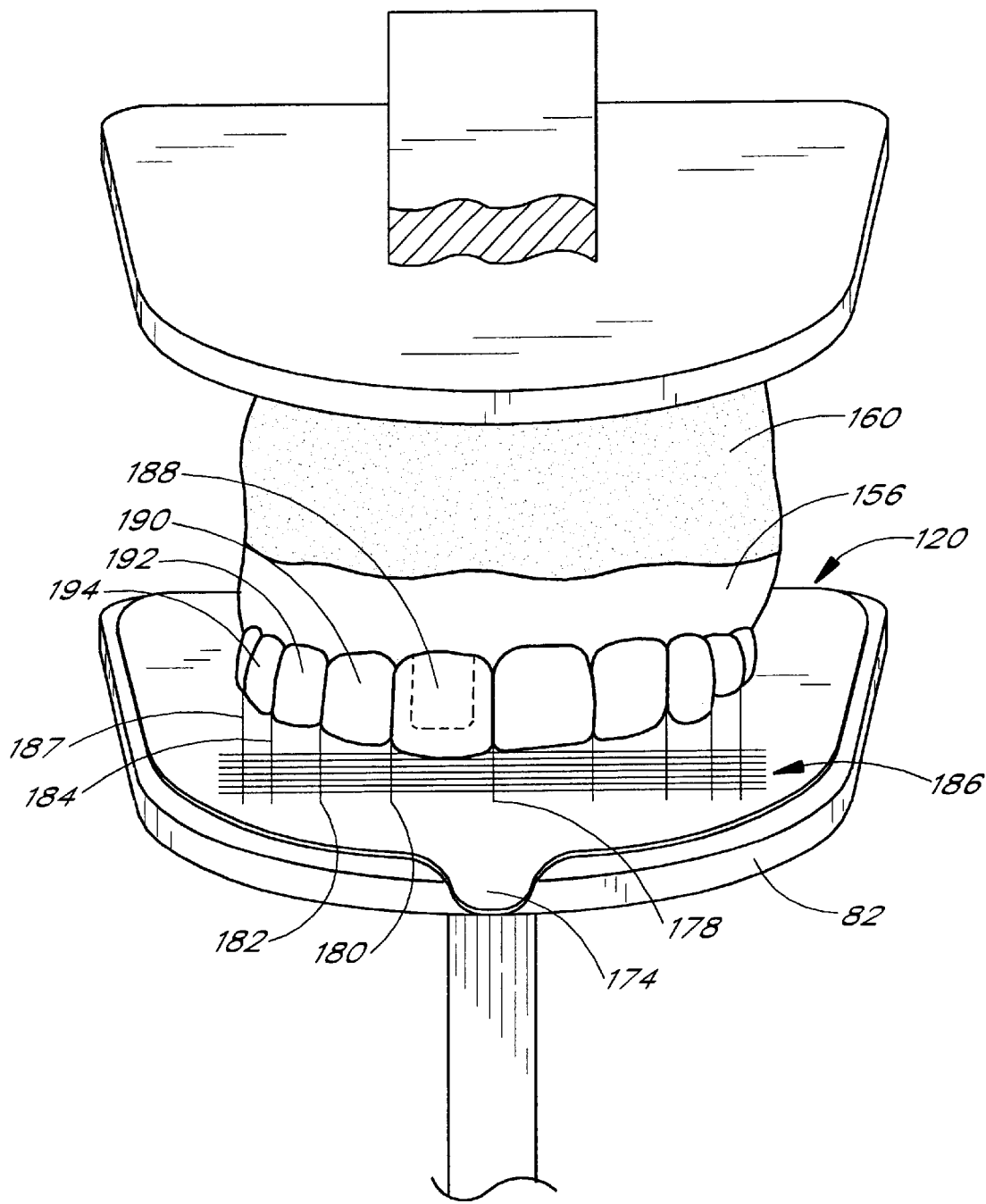
FIG. 16 is a schematic view illustrating the use of a waxing guide in relation to a maxillary dental cast.

Referring to FIGS. 14–16, there is illustrated a thin flat element 120 having markings 172 thereon that enable the element to serve as a guide for shaping artificial teeth. The element may be made of a thin sheet of paper or plastic that is intended to be disposable; or it may be made of stiff plastic, metal or other suitable material configured to be mounted to the platform 82 of FIG. 13, that is intended to be reuseable.

The guide preferably has a shape similar to a person's maxillary teeth. Optionally, the guide 120 has a forward tab 174 which facilitates mounting of the element on the support platform 82. Formed on the guide are a series of markings defining a series of parallel lines 126 that correspond to the spacing of the maxillary teeth. This includes a central line 178 to be oriented in the sagittal plane or midline of a dental cast. On each side of the central line is a line 180 marking the intersection between a central incisor 188 (FIG. 16) and a lateral incisor 190. Spaced further outwardly is a line 182 marking the intersection between the lateral incisor 190 and the adjacent canine 192. Spaced yet further outwardly is a line 184 marking the intersections between the canine tooth 192 and an adjacent bicuspid 194. Also shown is a line 187 marking the other side of that bicuspid.

Also formed on the guide are a series of spaced parallel incisal lines 186 which are perpendicular to the central line 178 which will guide moving or warping the incisal edges forward or backward. If the guide is to be used in a system that has a horizontally adjustable mounting platform 82, only a single incisal line is needed, but it is desirable to have the guide formed with a series of lines so that the same guide can be used with adjustable or non-adjustable platforms.

People of course have central incisors of different widths. Thus, it is desirable to have a series of guides with different widths between the central guide line and the adjacent line that marks the width of the incisor. For example, there may be provided a series of guides having widths varying from 7 mm up to 10 mm at half millimeter increments. For convenience, the particular size may be marked on the tab 174 at the forward end of the guide, as shown in FIG. 14, or somewhere on the guide. The markings shown in FIG. 14 indicate that the width of the central incisor is 7.5 mm, with lines provided for four teeth on each side of center.

FIG. 15 illustrates a guide having spacing when the central incisor is 10 mm wide, with markings for four teeth.

FIG. 16 illustrates the waxing guide 120 in use. The maxillary dental cast 156 of FIG. 11 has been mounted on the upper frame of a dental articulator, the upper index tray 34 has been removed from the mounting platform 82, and the waxing guide 120 has been positioned on the mounting platform 82 replacing the index tray 34. In positioning the guide 120 on the platform, care should be taken to properly align the central line 178 on the guide 120 with a central line 83 on the mounting platform. Similarly, the incisal lines 186 on the guide 120 should be aligned with the appropriate lines on the platform such as lines 92a in FIG. 6A. The dentist or technician can then form the desired artificial tooth utilizing the guide 120 as an indicator of the width of the anterior teeth. Since the guide is close to the cast, it is relatively easy for the dentist or technician when positioned centrally with respect to the guide and the dental cast to properly shape the teeth. Incidentally, the broken line showing on the central incisor 188 is intended to illustrate what might be a tooth portion on which a larger tooth is formed or shaped in wax.

As one example of the spacing on the guide 120, assume that the desired apparent width of the maxillary central incisor 188 as viewed from the front on the central line 178 is 10 mm. The golden ratio between the width of the lateral incisor 190 and the central incisor 188 is, as indicated above, 1:0.618. Thus, with a central incisor apparent width of 10 mm, the apparent width of the lateral incisor for desired aesthetics should be 6.18 mm. Similarly, the ratio between the lateral incisor and the adjacent canine tooth is 6.18 divided by 1.618 which equals 3.82. Adding those three numbers equals about 20 mm which is the distance between the central sagittal or midline line 178 and the lateral edge 184 of the canine tooth 192.

The spacing for the lines of guides employing a different apparent width for the maxillary central incisor is similarly calculated using the 1:1.618 ratio.

What is claimed is:

1. A device for forming artificial teeth comprising a waxing guide configured to be mounted on a platform beneath a maxillary dental cast;

said guide having a central marking on an upper surface and defining a central line extending toward forward and rearward edges of the element;

said guide having first and second incisal markings spaced laterally from said central marking and defining incisal lines, the space between the central marking and said first incisal marking, and the lateral space between the first and second incisal markings being in a desired aesthetic ratio, said spaces corresponding to desired apparent widths of artificial teeth on a dental cast when viewed from front of the cast on said central line and the guide is positioned beneath and aligned with the dental cast.

2. The device of claim 1, wherein the spacing between the central marking and the first incisal marking is greater than the spacing between the first incisal marking and the second incisal marking, and the ratio between the spaces is selected to provide what is deemed to be a desired proportion from an aesthetic standpoint.

3. The device of claim 2, wherein the ratio is about 1:1.618.

4. The device of claim 1, wherein said guide has a third marking spaced laterally from the second incisal marking and the ratio of the space between the central marking and the first incisal marking and the space between the first and second incisal markings is substantially the same as the ratio of the space between the first and second incisal markings and the space between the second and third markings.

5. The device of claim 4, in which said ratio is about 1:1.618.

6. The device of claim 1, wherein said element has one or more markings on its upper surface defining lines perpendicular to said central line and located to be aligned with an incisal line on said platform to be aligned with the incisal edge of the central maxillary teeth on the dental cast.

7. A method of facilitating the forming of artificial teeth or portions thereof comprising the steps of:
   mounting a maxillary dental cast on the upper frame of a dental articulator or other support;
   supporting on a platform a waxing guide spaced slightly beneath or positioned against the dental cast;
   aligning a guide on the platform so that a central line on the guide is aligned with the sagittal plane through the dental cast; and
   adding wax to partial teeth on the dental cast to shape maxillary anterior teeth, making the apparent lateral widths of the teeth as viewed from the front on the central line to be aligned with lines on the guide which have been selected to provide a desired aesthetic relationship.

8. The method of claim 7, wherein the desired relationship between a central incisor and an adjacent lateral incisor on the dental cast is the ratio of about 1:1.618, and the relationship between the lateral incisor and an adjacent canine tooth is at about that same ratio.

* * * * *